United States Patent [19]

Oka et al.

[11] Patent Number: 4,472,383
[45] Date of Patent: Sep. 18, 1984

[54] PEPTIDE DERIVATIVES, THEIR PRODUCTION AND USE

[75] Inventors: Yoshikazu Oka, Kawanishi; Kohei Nishikawa, Kyoto, both of Japan

[73] Assignee: Takeda Chemical Industries, Ltd., Osaka, Japan

[21] Appl. No.: 485,824

[22] Filed: Apr. 18, 1983

[30] Foreign Application Priority Data

Apr. 26, 1982 [JP] Japan ................................ 57-69897

[51] Int. Cl.$^3$ ...................... A61K 37/00; C07C 103/52
[52] U.S. Cl. ............................... 424/177; 260/112.5 R
[58] Field of Search .................. 424/177; 260/112.5 R

[56] References Cited

U.S. PATENT DOCUMENTS 4,105,776 8/1978 Ondetti et al. ...................... 424/274
4,256,761 3/1981 Suh et al. ............................ 424/282

FOREIGN PATENT DOCUMENTS 7477   2/1980  European Pat. Off. .
12401  6/1980  European Pat. Off. .
18104  10/1980 European Pat. Off. .
35868  9/1981  European Pat. Off. .

OTHER PUBLICATIONS

Central Patents Index Basic Abstracts Journal, Section B Farmdoc, 94293 D/51 BO2 Tana 11/04/80, J56145-274.

Abstract of the 102nd Annual Meeting of Pharmaceutical Society of Japan, p. 382, 3M4-4, (published on Mar. 10, 1982).

*Primary Examiner*—Delbert R. Phillips
*Attorney, Agent, or Firm*—Wegner & Bretschneider

[57] ABSTRACT

Novel peptide derivatives, inclusive of salts thereof, of the formula

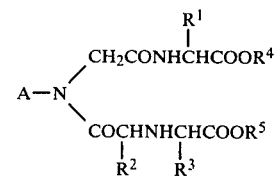

wherein A represents monocyclic or bicyclic hydrocarbon group, $R^1$ and $R^3$ are independently hydrogen, $C_{1-4}$ alkyl or phenyl-$C_{1-4}$ alkyl, and $R^2$, $R^4$ and $R^5$ are independently hydrogen or $C_{1-4}$ alkyl, have inhibitory activities of angiotensin converting enzyme and bradykinin decomposing enzyme, and are useful as antihypertensive agents.

13 Claims, No Drawings

PEPTIDE DERIVATIVES, THEIR PRODUCTION AND USE

This invention relates to novel peptide derivatives, which are useful as pharmaceuticals, and a process for producing the same. More particularly, this invention relates to novel peptide derivatives represented by the formula:

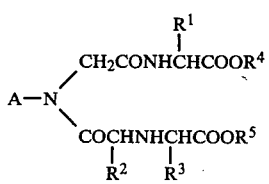

wherein A represents monocyclic or bicyclic hydrocarbon group, $R^1$ and $R^3$ are independently hydrogen, lower alkyl or aralkyl, $R^2$, $R^4$ and $R^5$ are independently hydrogen or lower alkyl, and salts thereof, to a process for producing the compounds (I) and to their use.

Referring to the above formula (I), the monocyclic hydrocarbon group representing by A includes saturated or unsaturated 3-membered to 8-membered hydrocarbon groups such as $C_{3-8}$ cycloalkyl (e.g. cyclopropyl, cyclobutyl, cyclopentyl, cyclohexyl, cycloheptyl, cyclooctyl), $C_{5-8}$ cycloalkenyl (e.g. cyclopentenyl, cyclohexenyl), cyclohexadienyl, phenyl, etc. The bicyclic hydrocarbon group represented by A includes naphthyl, dihydronaphthyl, tetrahydronaphthyl, indanyl, bicyclo[4,4,0]decyl, bicyclo[4,3,0]nonyl, bicyclo[3,3,0]octyl, bicyclo[2,2,1]heptyl, bicyclo[2,2,2]octyl etc. The bond of A may be situated in any attachable position of the cyclic hydrocarbon group.

The lower alkyl group represented by $R^1$, $R^2$, $R^3$, $R^4$ and $R^5$ includes alkyl groups of about 1 to 4 carbon atoms, such as methyl, ethyl, propyl, isopropyl, butyl, isobutyl, tert-butyl, etc. The aralkyl group represented by $R^1$ and $R^3$ includes phenyl-$C_{1-4}$ alkyl group such as benzyl, phenethyl, 3-phenylpropyl, 4-phenylbutyl, α-methylbenzyl, α-ethylbenzyl, etc.

The salts of compound (I) include such pharmaceutically acceptable salts as salts with inorganic acids, e.g. hydrochloride, hydrobromide, sulfate, nitrate, phosphate, etc., salts with organic acids, e.g. acetate, tartarate, citrate, fumarate, maleate, toluenesulfonate, methanesulfonate, etc., metal salts such as sodium salt, potassium salt, calcium salt, aluminum salt, etc., and salts with bases, e.g. ammonium salt, hydrazine salt, guanidine salt, triethylamine salt, dicyclohexylamine salt, quinine salt, cinchonine salt, etc.

In the above mentioned compounds (I), preferred embodiments are those of the formula (I) wherein A represents $C_{3-8}$ cycloalkyl or indanyl, $R^1$ and $R^3$ are independently phenyl-$C_{1-4}$ alkyl, $R^2$, $R^4$ and $R^5$ are independently hydrogen or $C_{1-4}$ alkyl, and phamaceutically acceptable salts thereof.

Among the compounds (I), further preferred are compounds wherein A is cyclopentyl or 2-indanyl, $R^1$ is benzyl, $R^2$ is methyl, $R^3$ is phenethyl, $R^4$ is hydrogen or $C_{1-4}$ alkyl, and $R^5$ is $C_{1-4}$ alkyl, and their pharmaceutically acceptable salts.

The compounds (I) of the present invention can be produced, for example, by subjecting a compound of the formula:

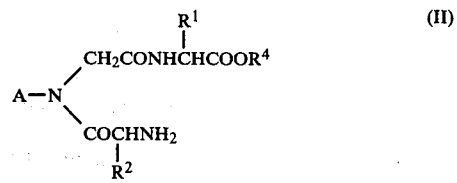

wherein all the symbols are as defined above, and a compound of the formula:

wherein $R^3$ and $R^5$ are as defined above, to condensation under reductive conditions, by condensing a compound of the formula:

wherein $R^{4'}$ is $C_{1-4}$ alkyl, and A and $R^1$ are as defined above, with a compound of the formula:

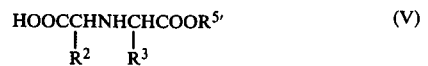

wherein $R^{5'}$ is $C_{1-4}$ alkyl, and $R^2$ and $R^3$ are as defined above, or a reactive derivative of its carboxyl function, or by condensing a compound of the formula:

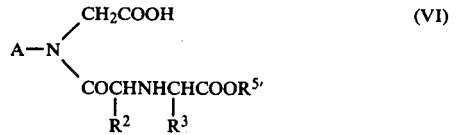

wherein all the symbols are as defined above, or a reactive derivative of its carboxyl function with a compound of the formula:

wherein $R^1$ and $R^{4'}$ are as defined above.

The reductive conditions for the reaction between compounds (II) and (III) may, for example, be catalytic reduction with the aid of a catalyst such as a metal catalyst (e.g. platinum, palladium, Raney nickel, rhodium, etc., unsupported or supported on a suitable carrier), reduction with a metal hydrogen compound (e.g. lithium aluminum hydride, lithium borohydride, lithium cyanoborohydride, sodium borohydride, sodium cyanoborohydride), reduction with sodium metal, magnesium metal or the like and an alcohol, reduction with a metal (e.g. iron, zinc) and an acid (e.g. hydrochloric acid, acetic acid), electrolytic reduction, or reduction with a reductase enzyme. The above reaction is generally conducted in the presence of water or an organic solvent (e.g. methanol, ethanol, ethyl ether, dioxane, methylene chloride, chloroform, benzene, toluene, dimethylformamide, dimethylacetamide). While the reaction temperature varies with the means of reduction employed, generally the reaction is preferably conducted at a temperature ranging from about −20° C. to about +100° C. Although this reaction can proceed in a satisfactory manner at ordinary pressure, it may also be carried out under elevated or reduced pressure, depending on the purpose.

Referring to the condensation reaction between compounds (IV) and (V) and between compounds (VI) and (VII), the reactive derivative of the carboxyl function of compound (V) and of compound (VI) is exemplified by acid halide (e.g. acid chloride, acid bromide), acid anhydride which is obtainable by eliminating one molecule of water from 2 molecules of (V) or (VI), and mixed anhydride obtainable by substituting the hydrogen atom of the carboxyl group with an ethoxycarbonyl, isobutyloxycarbonyl, benzyloxycarbonyl or the like. The reaction is generally conducted in a suitable solvent which may be any solvent as far as it does not interfere with the reaction. When (V) or (VI) is used as such, i.e. without prior converting it to a reactive derivative, the reaction is advantageously conducted in the presence of a dehydrating agent such as dicyclohexylcarbodiimide, carbonyldiimidazole, diethyl cyanophosphate, diphenylphosphorylazide, etc. These reactions may also be carried out in the presence of a base such as pyridine, picoline, triethylamine, sodium hydroxide, sodium carbonate, etc. The reaction temperature generally ranges from about −20° C. to about +150° C. and, in most cases, the reaction proceeds satisfactorily at room temperature.

Referring to the above formula (I), the compound in which $R^4$ and/or $R^5$ is hydrogen can also be produced by hydrolyzing a compound (I) wherein $R^4$ and/or $R^5$ is a group other than hydrogen.

This hydrolysis reaction is generally carried out in water, an organic solvent or a mixture thereof and in the presence or absence of an acid (e.g. hydrochloric acid, sulfuric acid, nitric acid, phosphoric acid, acetic acid, trifluoroacetic acid, benzenesulfonic acid, methanesulfonic acid, p-toluenesulfonic acid, etc.) or a base (e.g. ammonia, sodium hydroxide, potassium hydroxide, sodium carbonate, sodium hydrogen carbonate, triethylamine, pyridine, picoline). The reaction is generally conducted at a temperature ranging from about −20° C. to about +150° C. and, in most cases, proceeds satisfactorily at room temperature.

Contrary to the above case, the compound (I) wherein $R^4$ and/or $R^5$ is $C_{1-4}$ alkyl can also be produced by alkylating a compound (I) wherein $R^4$ and/or $R^5$ is hydrogen. Said alkylation includes, for example, a conventional esterification with a corresponding alcohol compound, or a usual alkylation by the use of diazomethane, alkyl halide or alkyl- or arylsulfonic acid ester of an alcohol compound or the like.

The product compound (I) or a salt thereof, thus produced, can be isolated from the reaction mixture by usual methods of separation and purification, such as extraction, concentration, neutralization, filtration, recrystallization, column chromatography and/or thin layer chromatography, etc.

When the compound of the formula (I) contains asymmetric carbon atoms, there exist a plurality of optical isomers. Such individual isomers and mixtures thereof naturally fall within the scope of this invention. These isomers, if desired, may be produced individually. Thus, by conducting the above reactions using one optical isomer of starting compounds obtained by previous optical separation, the corresponding isomer of the formula (I) can be produced. When at least one of the starting compounds is a racemic compound, the compound (I) is generally obtained as a mixture of isomers but these isomers can be separated into individual isomers by a conventional separation technique, such as salt formation using an optically active base (e.g. cinchonine, cinchonidine, quinine, quinidine), various chromatographic processes, fractional recrystallization, etc.

Referring to the carbon atoms carrying the substituents $R^1$, $R^2$ and $R^3$ in these optical isomers, generally the S-configurated isomers are preferable to the R-configurated isomers in physiological activity.

The peptide derivatives represented by the formula (I) and the salts thereof, exhibit inhibitory activities on angiotensin converting enzyme, bradykinin decomposing enzyme (kininase) in animals, in particular, mammals and are useful, for example, as drugs for diagnosis, prevention or treatment of hypertension. The compounds (I) are of low toxicity, well absorbed even on oral administration and highly stable. Therefore, when they are used as the above-mentioned drugs, they can safely be administered orally or parenterally, per se or in admixture with suitable pharmaceutically acceptable carriers, excipients or diluents in various pharmaceutical formulations such as powders, granules, tablets, capsules, injectable solutions, etc. While the dosage level generally varies depending upon the conditions of the diseases to be treated as well as the administration route used, for example, in the treatment of hypertension in adult human, the compounds may be administered orally at a single dose of about 0.02–20 mg/kg, preferably about 0.2–2. mg/kg, or intraveneously at about 0.002–0.2 mg/kg, preferably about 0.02–0.2 mg/kg, about 2 to 5 times per day according to the conditions.

The starting compounds (II), (IV), (V) and (VI) for the production processes described above can be prepared by, for example, the process shown by the following reaction schema:

A—NHCH$_2$COOBu$^t$ $\xrightarrow{\text{HBr}}$ A—NHCH$_2$COOH $\xrightarrow{\text{(VII)}}$ (VIII)                             (IX)

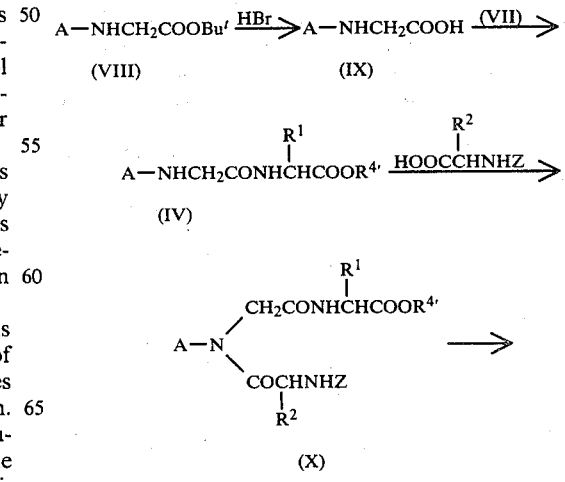

-continued

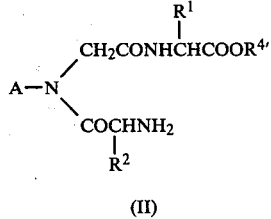

(II)

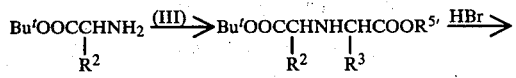

(XI)　　　　　　(XII)

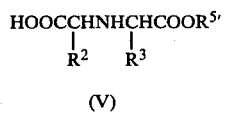

(V)

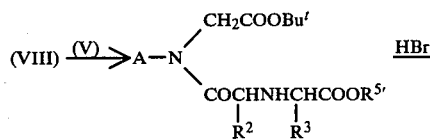

(XIII)

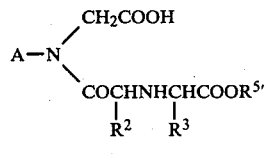

(VI)

In the formulae, A, $R^1$, $R^2$, $R^3$, $R^{4'}$ and $R^{5'}$ are as defined above; Z is benzyloxycarbonyl; $Bu^t$ is tert-butyl.

In the above reaction schema, the reactions (VIII)→(IX), (XII)→(V) and (XIII)→(VI) are each carried out by acting a solution of hydrogen bromide in acetic acid at room temperature, and the reactions (IX)→(IV), (IV)→(X) and (VIII)→(XIII) are each carried out under the same conditions as those described for the reaction of (IV) with (V) and the reaction of (VI) with (VII). The reaction of (X)→(II) is carried out by catalytic reduction using palladium-carbon as a catalyst at ordinary temperature and ordinary pressure, and the reaction of (VIII)→(XIII) is conducted in the same manner as in the reaction of (II) with (III) described above.

The invention will be further illustrated in more detail by the following reference examples, embodiment examples, test examples and dosage form examples, which however, are by no means limitative of the present invention.

REFERENCE EXAMPLE 1

2-Indanone (3.6 g) and glycyl-L-phenylalanine tert-butyl ester (7.3 g) are dissolved in 50 ml of methanol and 3 g of sodium cyanoborohydride is added in small portions at room temperature. Then, 0.5 ml of ethanolic solution of 7N hydrogen chloride (0.5 ml) is added dropwise and the mixture is allowed to stand at room temperature overnight. To the reaction mixture are added 50 ml of methanol and 200 ml of 10% phosphoric acid, followed by extraction with a mixture of ether (100 ml) and petroleum ether (100 ml). The aqueous layer is made neutral with sodium hydrogen carbonate and extracted twice with 200 ml portions of ethyl acetate. The extracts are combined, dried over anhydrous magnesium sulfate, and distilled to remove the solvent, whereby a yellow-colored oil is obtained. This product is dissolved in ether and a solution of 2 g of oxalic acid in a small quantity of ethanol is added. The resulting crystalline precipitate is collected by filtration and dried to give 5.4 g of N-(2-indanyl)glycyl-L-phenylalanine tert-butyl ester oxalate. The product is added to a mixture of 20 ml of methanol and 100 ml of water and made alkaline by dropwise addition of 1N sodium hydroxide with stirring. The crystalline precipitate is collected by filtration and dried to give 4 g of free N-(2-indanyl)glycyl-L-phenylalanine tert-butyl ester melting at 117°–120° C.

IR Spectrum $\nu_{max}^{Nujol}$ cm$^{-1}$: 1740, 1640 (C=O).

Elemental Analysis for $C_{24}H_{30}N_2O_3 \cdot \frac{1}{2}H_2O$. Calcd.: C,71.43; H,7.74; N,6.94. Found: C,71.35; H,7.33; N,6.81.

REFERENCE EXAMPLE 2

N-Carbobenzoxy-L-alanine (3.5 g) and triethylamine (1.6 g) are dissolved in 50 ml of tetrahydrofuran, followed by dropwise addition of 1.7 g of ethyl chlorocarbonate with stirring at −15° C. After completion of addition, the mixture is stirred for 15 minutes and, a solution of 3.9 g of N-(2-indanyl)glycyl-L-phenylalanine tert-butyl ester in 100 ml of chloroform is added dropwise at −10° C. The mixture is stirred at room temperature for one hour and poured into 50 ml of water. The chloroform layer is separated and distilled. The residue is dissolved in 200 ml of ethyl acetate. The solution is washed twice with 50 ml portions of 1N sodium hydroxide, once with 50 ml of water, twice with 50 ml portions of 10% aqueous solution of phosphoric acid, and once with 50 ml of water in that order. It is then dried over anhydrous magnesium sulfate and distilled to give 5.6 g of N-carbobenzoxy-L-alanyl-N-(2-indanyl)glycyl-L-phenylalanine tert-butyl ester as an oil.

IR Spectrum $\nu_{max}^{Neat}$ cm$^{-1}$: 3300(NH), 1720, 1700, 1680, 1640 (C=O).

NMR Spectrum (CDCl$_3$)δ: 1.3–1.5(12H,CH$_3$×4), 2.8–3.2(6H,CH$_2$×3), 5.1(single,2H,

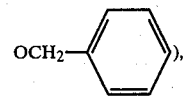

7.0–7.3(14H, phenyl protons).

REFERENCE EXAMPLE 3

N-Carbobenzoxy-L-alanyl-N-(2-indanyl)glycyl-L-phenylalanine tert-butyl ester (5.6 g) is dissolved in 100 ml of methanol and after addition of 0.93 g of oxalic acid and 2 g of 10% palladium-carbon (water content 50%), catalytic reduction is carried out at ordinary temperature and ordinary pressure. After the reaction, the catalyst is filtered off and the filtrate is distilled off under reduced pressure. The residue is shaken well with 200 ml of ethyl ether and 100 ml of petroleum ether and then allowed to stand. The supernatant is removed by decantation and, on addition of 200 ml of petroleum ether to the precipitate, L-alanyl-N-(2-indanyl)glycyl-L-phenylalanine tert-butyl ester oxalate solidifies. This product is collected by filtration and dried to give 4 g of colorless powder.

Elemental Analysis for $C_{27}H_{35}N_3O_4 \cdot C_2H_2O_4 \cdot H_2O$. Calcd.: C,60.72; H,6.85; N,7.33. Found: C,60.32; H,6.82; N,7.02.

$[\alpha]_D^{24} +9.8°$ (c=1, methanol).

REFERENCE EXAMPLE 4

Cyclopentanone (10 g) and glycine ethyl ester hydrochloride (21.6 g) are dissolved in 200 ml of methanol, and 7.48 g of sodium cyanoborohydride is added in small portions with stirring at room temperature. The mixture is further stirred at room temperature for 3 hours and the reaction mixture is concentrated under reduced pressure. To the residue is added 500 ml of water and the mixture is adjusted to pH 10 with diluted sodium hydroxide solution and extracted with 300 ml of ethyl acetate. The extract is washed with saturated aqueous sodium chloride and dried over sodium sulfate. The solvent is then distilled off under reduced pressure and the resulting oily product is dissolved in 200 ml of ether, followed by addition of 10 ml of 10% alcoholic hydrochloride, whereupon crystals immediately separates out. The crystals are collected by filtration to give 12.7 g of N-cyclopentylglycine ethyl ester hydrochloride as colorless needles melting at 174°–175° C.

REFERENCE EXAMPLE 5

N-Carbobenzoxy-L-alanine (11.4 g) and triethylamine (6.7 ml) are dissolved in 100 ml of tetrahydrofuran and under stirring at −10° C., 6.5 ml of isobutyl chlorocarbonate is added in small portions. Then, at −10° C. to −5° C., a solution of N-cyclopentylglycine ethyl ester hydrochloride (10 g) and triethylamine (6.7 ml) in chloroform (100 ml) is added and the mixture is allowed to stand at room temperature overnight. The reaction mixture is filtered and the filtrate is concentrated. To the residue is added 300 ml of water, followed by extraction with 200 ml of ethyl acetate. The ethyl acetate layer is washed with 5% hydrochloric acid, aqueous sodium hydrogen carbonate and water in that order and dried over sodium sulfate. Removal of the solvent by distillation gives an oil, which is separated and purified by column chromatography using 150 g of silica gel. The fractions eluted with toluene-ethyl acetate (5:1) are collected to give 11 g of N-carbobenzoxy-L-alanyl-N-cyclopentylglycine ethyl ester as an oil. This product (10 g) is dissolved in 100 ml of ethanol, then 16 ml of 2N sodium hydroxide is added, and the mixture is stirred at room temperature for 5 hours. The reaction mixture is concentrated and the concentrate is diluted with 100 ml of water and acidified with 10% hydrochloric acid, whereupon an oil separates out. This oil is extracted with 300 ml of ethyl acetate and the extract is washed with water, dried and concentrated to give 8 g of N-carbobenzoxy-L-alanyl-N-cyclopentylglycine as colorless oil.

IR Spectrum $v_{max}^{Neat}$ cm$^{-1}$: 3700–2200(COOH), 1720(N—CO—O), 1640(N—CO—O).

REFERENCE EXAMPLE 6

N-Carbobenzoxy-L-alanyl-N-cyclopentylglycine (4 g) and L-phenylalanine tert-butyl ester (2.4 g) are dissolved in 20 ml of dimethylformamide and under ice-cooling and stirring, a solution of 1.9 g of diethyl cyanophosphate in 5 ml of dimethylformamide is added, followed by addition of 1.6 ml of triethylamine. The mixture is stirred at room temperature for 3 hours. Then, 200 ml of ice water is added and the mixture is extracted twice with 50 ml portions of ethyl acetate. The extract is washed with 1N hydrochloric acid and water and dried. The solvent is then distilled off under reduced pressure to give 6.7 g of N-carbobenzoxy-L-alanyl-N-cyclopentylglycyl-L-phenylalanine tert-butyl ester as colorless oil.

IR Spectrum $v_{max}^{Neat}$ cm$^{-1}$: 3300(NH), 1720, 1710, 1650 (C═O).

REFERENCE EXAMPLE 7

N-Carbobenzoxy-L-alanyl-N-cyclopentylglycyl-L-phenylalanine tert-butyl ester (6.7 g) is dissolved in 100 ml of methanol, and according to the procedure of Reference Example 3, catalytic reduction is conducted in the presence of 1 g of oxalic acid and 1.5 g of 5% palladium-carbon (water content 50%). By the above procedure there is obtained 5.5 g of L-alanyl-N-cyclopentylglycyl-L-phenylalanine tert-butyl ester oxalate as colorless powder.

Elemental Analysis for $C_{25}H_{35}N_3O_4 \cdot C_2H_2O_4 \cdot 3/2H_2O$. Calcd.: C,56.16; H,7.54; N,7.66. Found: C,56.19; H,7.52; N,7.41.

$[\alpha]_D^{22} -20.4°$ (c=0.935, methanol).

EXAMPLE 1

L-Alanyl-N-(2-indanyl)glycyl-L-phenylalanine tert-butyl ester oxalate (4 g) is dissolved in 30 ml of ethanol, followed by addition of 0.9 g of sodium acetate, 2 g of acetic acid, 4 g of ethyl 2-oxo-4-phenylbutyrate and 8 g of Molecular Sieves 3A in that order. Then, a suspension of 8 g Raney nickel in 20 ml of ethanol is added along with ethanol, and catalytic reduction is carried out at ordinary temperature and ordinary pressure. After absorption of hydrogen has ceased, the supernatant is separated by decantation, while the precipitate is washed with 2 or 3 portions of ethanol. The washings are combined with the supernatant and the whole solution is concentrated under reduced pressure. The residue is dissolved in 300 ml of ethyl acetate and an aqueous solution of sodium hydrogen carbonate is added. The mixture is filtered using 10 g of diatomaceous earth as a filtration aid. The ethyl acetate layer is taken from the filtrate, washed with water and dried over anhydrous magnesium sulfate. The solvent is then distilled off to give an oil. This product is purified by column chromatography on silica gel (200 g) with the solvent system of benzene and acetone (20:1 to 10:1). From the first group of fractions containing the corresponding R-configurated ester, 0.2 g of N-[1(R)-ethoxycarbonyl-3-phenylpropyl]-L-alanyl-N-(2-indanyl)glycyl-L-phenylalanine tert-butyl ester is recovered as colorless syrup.

IR Spectrum $v_{max}^{Neat}$ cm$^{-1}$: 3300(NH), plural absorptions at 1640–1720(C═O).

NMR Spectrum (CDCl$_3$)δ: 1.1–1.6(15H,CH$_3$×5), 4.1 (quartet,J=7 Hz,2H, methylene of ethyl ester), 6.8–7.4 (14H, phenyl protons).

Mass Spectrum m/e: 655(M+).

From the second fractions containing the corresponding S-configurated ester, 1.9 g of N-[1(S)-ethoxycarbonyl-3-phenylpropyl]-L-alanyl-N-(2-indanyl)glycyl-L-phenylalanine tert-butyl ester is recovered as colorless syrup.

IR Spectrum $v_{max}^{Neat}$ cm$^{-1}$: 3300(NH), 1640–1720(C═O).

Elemental Analysis for $C_{39}H_{49}N_3O_6$. Calcd.: C,71.42; H,7.53; N,6.41. Found: C,71.30; H,7.49; N,6.16.

NMR Spectrum (CDCl$_3$)δ: 1.15–1.50(15H,CH$_3$×5), 4.20(quartet,J=7 Hz, methylene of ethyl ester), 6.90–7.35 (14H, phenyl protons).

Mass Spectrum m/e: 655(M$^+$).

[α]$_D^{24}$ −5.0° (c=0.5, methanol).

EXAMPLE 2

N-[1(R)-Ethoxycarbonyl-3-phenylpropyl]-L-alanyl-N-(2-indanyl)glycyl-L-phenylalanine tert-butyl ester (0.2 g) is dissolved in 0.5 ml of acetic acid and shaken with 1 ml of 30% hydrogen bromide in acetic acid for 10 minutes, followed by addition of 50 ml of ether and 50 ml of petroleum ether. The supernatant is decanted off and petroleum ether is added to the residue. The solid substance is collected by filtration and dried to give 0.18 g of N-[1(R)-ethoxycarbonyl-3-phenylpropyl]-L-alanyl-N-(2-indanyl)glycyl-L-phenylalanine hydrobromide as powder.

Elemental Analysis for C$_{35}$H$_{41}$N$_3$O$_6$.HBr.H$_2$O. Calcd.: C,60.17; H,6.35; N,6.02. Found: C,60.00; H,6.33; N,5.93.

Mass Spectrum m/e: 599(M$^+$)

[α]$_D^{24}$ −7.5° (c=1, methanol).

NMR Spectrum (d$_6$-DMSO)δ: 1.2–1.5(6H,CH$_3$×2), 4.3 (quartet, J=5 Hz, methylene of ethyl ester), 7.1–7.3 (14H, phenyl protons).

EXAMPLE 3

N-[1(S)-Ethoxycarbonyl-3-phenylpropyl]-L-alanyl-N-(2-indanyl)glycyl-L-phenylalanine tert-butyl ester (1.8 g) is dissolved in 2 ml of acetic acid, and 3 ml of 30% hydrogen bromide in acetic acid is added. The mixture is reacted at room temperature for 10 minutes. The reaction mixture is shaken with 300 ml of ether and allowed to stand. The ether is then decanted off and to the precipitate is added ethyl acetate, whereby 1.35 g of N-[1(S)-ethoxycarbonyl-3-phenylpropyl]-L-alanyl-N-(2-indanyl)glycyl-L-phenylalanine hydrobromide is obtained as colorless prisms melting at 177°–181° C. (decomposition).

Elemental Analysis for C$_{35}$H$_{41}$N$_3$O$_6$.HBr. Calcd.: C,61.76; H,6.22; N,6.17. Found: C,61.54; H,6.30; N,6.12.

IR Spectrum ν$_{max}^{Nujol}$ cm$^{-1}$: 3220(NH), 1740, 1710, 1670, 1640(C=O).

Mass Spectrum m/e: 599(M$^+$).

[α]$_D^{24}$ +19.5° (c=1, methanol).

EXAMPLE 4

L-Alanyl-N-cyclopentylglycyl-L-phenylalanine tert-butyl ester oxalate (5.5 g), butyl 2-oxo-4-phenylbutyrate (5.5 g), sodium acetate (1.8 g), acetic acid (4.4 g), Raney nickel (6 g) and Molecular Sieves 3A (10 g) are suspended in 100 ml of ethanol. The suspension is reacted and treated in the same manner as Example 1, followed by purification by column chromatography. From the first group of fractions containing the corresponding R-configurated ester, 1 g of N-[1(R)-butoxycarbonyl-3-phenylpropyl]-L-alanyl-N-cyclopentylglycyl-L-phenylalanine tert-butyl ester is recovered as colorless oil.

IR Spectrum ν$_{max}^{Neat}$ cm$^{-1}$: 3300(NH), 1720, 1640(C=O).

NMR Spectrum (CDCl$_3$)δ: 1.0–1.6(19H,CH$_3$×5+CH$_2$CH$_2$) 7.25(10H,phenyl).

Mass Spectrum m/e: 635(M$^+$).

From the second group of fractions containing the corresponding S-configurated ester, 1.1 g of N-[1(S)-butoxycarbonyl-3-phenylpropyl]-L-alanyl-N-cyclopentylglycyl-L-phenylalanine tert-butyl ester is recovered as colorless oil.

IR Spectrum ν$_{max}^{Neat}$ cm$^{-1}$: 3300(NH), 1720, 1640–1680 (C=O).

NMR Spectrum (CDCl$_3$)δ: 1.0–1.7(19H,CH$_3$×5+CH$_2$CH$_2$), 7.2(10H, phenyl).

Mass Spectrum m/e: 635(M$^+$).

EXAMPLE 5

N-[1(R)-Butoxycarbonyl-3-phenylpropyl]-L-alanyl-N-cyclopentylglycyl-L-phenylalanine tert-butyl ester (1 g) is dissolved in 14 ml of 3.4N hydrogen chloride in ethyl acetate, followed by addition of 2 ml of acetone. Then, 10 ml of ether is added and the solvent is decanted off. The residue is dried under reduced pressure to give 0.8 g of N-[1(R)-butoxycarbonyl-3-phenylpropyl]-L-alanyl-N-cyclopentylglycyl-L-phenylalanine hydrochloride as colorless powder.

Elemental Analysis for C$_{33}$H$_{45}$N$_3$O$_6$.HCl. Calcd.: C,64.32; H,7.53; N,6.82. Found: C,64.20; H,7.88; N,6.64.

IR Spectrum ν$_{max}^{KBr}$ cm$^{-1}$: 3700–2200(COOH), 1740, 1680, 1650(C=O).

[α]$_D^{24}$ −14.1° (c=1, ethanol).

EXAMPLE 6

N-[1(S)-Butoxycarbonyl-3-phenylpropyl]-L-alanyl-N-cyclopentylglycyl-L-phenylalanine tert-butyl ester (1.1 g) is dissolved in 15 ml of 3.4N hydrogen chloride in ethyl acetate and the solution is allowed to stand at room temperature for 8 hours. The reaction mixture is distilled under reduced pressure. To the residue is added 20 ml of ether and the mixture is allowed to stand, whereupon 0.85 g of N-[1(S)-butoxycarbonyl-3-phenylpropyl]-L-alanyl-N-cyclopentylglycyl-L-phenylalanine hydrochloride is deposited as colorless crystals melting at 161°–164° C.

Elemental Analysis for C$_{33}$H$_{45}$N$_3$O$_6$.HCl. Calcd.: C,64.32; H,7.53; N,6.82. Found: C,64.13; H,7.65; N,6.91.

IR Spectrum ν$_{max}^{KBr}$ cm$^{-1}$: 3600–2300(COOH), 1740, 1680, 1660(C=O).

[α]$_D^{24}$ +10.8° (c=0.9, ethanol).

EXPERIMENT

Effect of Present Compounds against Hypertensive Activity of Angiotensin I

EXPERIMENTAL METHOD

Male rats (Sprague-Dawley) weighing 250 g to 350 g which were fed under free access to drinking water and feeds were used as experimental animals. The rats were anesthetized with intraperitoneal administration of pentobarbital sodium (50 mg/kg) on the day before the test day and a polyethylene tube was inserted into each of the femoral artery for measurement of blood pressure and the femoral vein for injection of angiotensin I and II, and then the tubes were fixed.

On the test day, an average blood pressure in the control phase was recorded on an electric hemodynamometer (MP-4T model manufactured by Nippon Koden, Japan) and thereafter angiotensin I and then angiotensin II were injected through the femoral vein at a dose of 300 ng/kg and 100 ng/kg respectively, to measure the hypertensive activity. Then, 13.8 μM/kg of the compound of this invention was administered orally as an aqueous solution or an aqueous gum arabic suspension, and 20, 60 and 120 minutes after the administration, angiotensin I and II were injected repeatedly to trace hypertensive reactions. In calculating the percent inhibition to the hypertensive activity of angiotensin I, the percent inhibitory value was corrected based on the variation with time in the hypertensive reaction by angiotensin II.

TEST RESULT

The test results obtained with respect to the compounds of Examples 3 and 6 are shown in Table below.

TABLE

| Example No. of Tested Compound | Percent Inhibition (%) against Hypertensive Reaction by Angiotensin I | | |
|---|---|---|---|
| | After 20 min. | After 60 min. | After 120 min. |
| 3 | 67 | 73 | 77 |
| 6 | 72 | 84 | 72 |

PREPARATION EXAMPLE

The compounds (I) of the present invention, when used for the treatment of hypertension for example, may be administered in, for example, the following formulations.

1. Tablets

| (1) | N—[1(S)-Ethoxycarbonyl-3-phenylpropyl]-L-alanyl-N—(2-indanyl)glycyl-L-phenylalanine hydrobromide | 10 g |
|---|---|---|
| (2) | Lactose | 90 g |
| (3) | Corn Starch | 29 g |
| (4) | Magnesium Stearate | 1 g |
| | for 1000 tablets | 130 g |

The above ingredients (1), (2) and 17 g of (3) are blended, and granulated using a paste prepared from 7 g of (3). Five grams of (3) and the ingredient (4) are added to the resulting granules and the mixture is compressed by a tabletting machine to prepare 1000 tablets having a diameter 7 mm each containing 10 mg of the ingredient (1).

2. Capsules

| (1) | N—[1(S)-Butoxycarbonyl-3-phenylpropyl]-L-alanyl-N—cyclopentylglycyl-L-phenylalanine hydrochloride | 10 g |
|---|---|---|
| (2) | Lactose | 135 g |
| (3) | Cellulose Fine Powder | 70 g |
| (4) | Magnesium Stearate | 5 g |
| | for 1000 capsules | 220 g |

All of the above components are blended and encapsulated into Gelatin Capsule No. 3 (IX Japanese Pharmacopoiea) to prepare 1000 capsules each containing 10 mg of the ingredient (1).

3. Injectable Solution

| (1) | N—[1(S)-Butoxycarbonyl-3-phenylpropyl]-L-alanyl-N—cyclopentylglycyl-L-phenylalanine hydrochloride | 10 g |
|---|---|---|
| (2) | Sodium Chloride | 9 g |
| (3) | Chlorobutanol | 5 g |

All of the above ingredients are dissolved in 1000 ml of distilled water and charged into 1000 brown ampules each containing 1 ml of the solution. The air in the ampules are replaced with nitrogen gas and the ampules are sealed. The entire preparation steps are conducted under sterile conditions.

What is claimed is:

1. A compound of the formula:

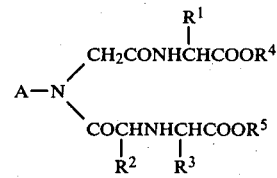

wherein A is a $C_{3-8}$ cycloalkyl, $C_{5-8}$ cycloalkenyl, cyclohexadienyl, phenyl, naphthyl, dihydronaphthyl, tetrahydronaphthyl, indanyl, bicyclo[4,4,0]decyl, bicyclo[4,3,0]nonyl, bicyclo[3,3,0]octyl, bicyclo[2,2,1]heptyl or bicyclo[2,2,2]octyl group, $R^1$ and $R^3$ are independently hydrogen, $C_{1-4}$ alkyl or phenyl-$C_{1-4}$ alkyl, and $R^2$, $R^4$ and $R^5$ are independently hydrogen or $C_{1-4}$ alkyl, or a pharmaceutically acceptable salt thereof.

2. A compound according to claim 1, wherein A is $C_{3-8}$ cycloalkyl or indanyl.

3. A compound according to claim 1, wherein $R^1$ is phenyl-$C_{1-4}$ alkyl.

4. A compound according to claim 1, wherein $R^2$ is $C_{1-4}$ alkyl.

5. A compound according to claim 1, wherein $R^3$ is phenyl-$C_{1-4}$ alkyl.

6. A compound according to claim 1, wherein $R^4$ is hydrogen.

7. A compound according to claim 1, wherein $R^5$ is $C_{1-4}$ alkyl.

8. A compound according to claim 1, wherein A is 2-indanyl, $R^2$ is methyl, $R^3$ is β-phenethyl and $R^5$ is ethyl.

9. The compound according to claim 1, which is N-[1-butoxycarbonyl-3-phenylpropyl]-L-alanyl-N-cyclopentylglycyl-L-phenylalanine.

10. The compound according to claim 1, which is N-[1-ethoxycarbonyl-3-phenylpropyl]-L-alanyl-N-(2-indanyl)glycyl-L-phenylalanine.

11. The compound according to claim 1, which is N-[1(S)-ethoxycarbonyl-3-phenylpropyl]-L-alanyl-N-(2-indanyl)glycyl-L-phenylalanine.

12. A pharmaceutical composition suitable for prevention or treatment of hypertension which comprises, as an active ingredient, an effective antihypertensive amount of a compound of the formula:

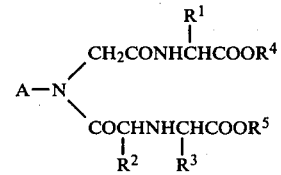

wherein A is a $C_{3-8}$ cycloalkyl, $C_{5-8}$ cycloalkenyl, cyclohexadienyl, phenyl, naphthyl, dihydronaphthyl, tetrahydronaphthyl, indanyl, bicyclo[4,4,0]decyl, bicyclo[4,3,0]nonyl, bicyclo[3,3,0]octyl, bicyclo[2,2,1]heptyl or bicyclo[2,2,2]octyl group, $R^1$ and $R^3$ are independently hydrogen, $C_{1-4}$ alkyl or phenyl-$C_{1-4}$ alkyl, and R², R⁴ and R⁵ are independently hydrogen or C₁₋₄ alkyl, or a pharmaceutically acceptable salt thereof, and a pharmaceutically acceptable carrier, excipient or diluent therefor.

13. A method for prevention or treatment of hypertension in a mammal, which comprises administering to said mammal an effective antihypertensive amount of a compound of the formula:

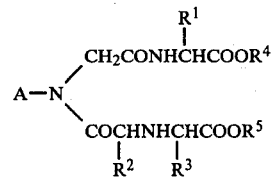

wherein A is a $C_{3-8}$ cycloalkyl, $C_{5-8}$ cycloalkenyl, cyclohexadienyl, phenyl, naphthyl, dihydronaphthyl, tetrahydronaphthyl, indanyl, bicyclo[4,4,0]decyl, bicyclo[4,3,0]nonyl, bicyclo[3,3,0]octyl, bicyclo[2,2,1]heptyl or bicyclo[2,2,2]octyl group, R¹ and R³ are independently hydrogen, $C_{1-4}$ alkyl or phenyl-$C_{1-4}$ alkyl, and R², R⁴ and R⁵ are independently hydrogen or $C_{1-4}$ alkyl, or a pharmaceutically acceptable salt thereof.

* * * * *